United States Patent
Sun et al.

(10) Patent No.: US 10,604,478 B1
(45) Date of Patent: Mar. 31, 2020

(54) METHOD FOR PRODUCING TAURINE AND METHOD FOR REMOVING IMPURITY FROM REACTION SYSTEM FOR PRODUCING TAURINE

(71) Applicant: HUBEI GRAND LIFE SCIENCE AND TECHNOLOGY CO., LTD., Huangshi (CN)

(72) Inventors: Huajun Sun, Huangshi (CN); Hongbo Peng, Huangshi (CN); Ruyong Jiang, Huangshi (CN); Chen Guo, Huangshi (CN); Zhiqiang Qian, Huangshi (CN)

(73) Assignee: HUBEI GRAND LIFE SCIENCE AND TECHNOLOGY CO., LTD., Huangshi (CN)

( * ) Notice: Subject to any disclaimer, the term of this patent is extended or adjusted under 35 U.S.C. 154(b) by 0 days.

(21) Appl. No.: 16/548,565

(22) Filed: Aug. 22, 2019

(30) Foreign Application Priority Data

Jun. 28, 2019  (CN) .......................... 2019 1 0574419

(51) Int. Cl.
| | | |
|---|---|---|
| *C07C 303/44* | (2006.01) | |
| *C07C 303/22* | (2006.01) | |
| *C07C 303/32* | (2006.01) | |
| *C07C 303/02* | (2006.01) | |
| *C07C 309/08* | (2006.01) | |
| *C07C 309/14* | (2006.01) | |
| *B01D 15/36* | (2006.01) | |

(52) U.S. Cl.
CPC .......... *C07C 303/44* (2013.01); *C07C 303/02* (2013.01); *C07C 303/22* (2013.01); *C07C 303/32* (2013.01); *B01D 15/363* (2013.01); *C07C 309/08* (2013.01); *C07C 309/14* (2013.01)

(58) Field of Classification Search
None
See application file for complete search history.

(56) References Cited

U.S. PATENT DOCUMENTS 2,693,488 A * 11/1954 Sexton ..................... B01J 39/00
562/104

FOREIGN PATENT DOCUMENTS

JP     H07206804      *  8/1995

OTHER PUBLICATIONS

"Ion Exchange Chromatography" Manual by GE Healthcare, downloaded from https://cdn.gelifesciences.com/dmm3bwsv3/AssetStream.aspx?mediaformatid=10061&destinationid=10016&assetid=13101 on Oct. 11, 2019, dated Jan. 2016 (Year: 2016).*
Song ("Taurine and Glycine Uptake onto a Strongly Basic Anion-exchange Resin Adsorption Science and Technology", vol. 24, No. 9, 2006, p. 737-748) (Year: 2006).*

* cited by examiner

*Primary Examiner* — Amy C Bonaparte
(74) *Attorney, Agent, or Firm* — Westman, Champlin & Koehler, P.A.; Z. Peter Sawicki; Amanda M. Prose

(57) ABSTRACT

Provided is a method for producing taurine including: providing a reaction solution comprising alkali metal taurinate and/or alkali metal isethionate, passing at least a portion of the reaction solution through a column of basic anion exchange resin, adsorbing anions of alkali metal taurinate and/or alkali metal isethionate to the basic anion exchange resin, and collecting an eluate comprising at least one impurity, desorbing anions of alkali metal taurinate and/or alkali metal isethionate from the basic anion exchange resin with an alkaline solution, and collecting a desorption liquid comprising alkali metal taurinate and/or alkali metal isethionate, subjecting the desorption liquid comprising alkali metal taurinate to acidification or subjecting the desorption liquid comprising alkali metal isethionate to aminolysis and acidification, thereby obtaining taurine.

20 Claims, No Drawings

METHOD FOR PRODUCING TAURINE AND METHOD FOR REMOVING IMPURITY FROM REACTION SYSTEM FOR PRODUCING TAURINE

CROSS-REFERENCE TO RELATED APPLICATION

This application claims a priority to and benefits of Chinese Patent Application Serial No. 201910574419.0, filed with the National Intellectual Property Administration of P. R. China on Jun. 28, 2019, the entire content of which is incorporated herein by reference.

FIELD

The present disclosure relates to the field of taurine production technologies, and more particularly to a method for producing taurine and a method for removing an impurity from a reaction system for producing taurine.

BACKGROUND

Taurine is a specific amino acid exhibiting a variety of physiological functions, such as of promoting brain and mental developments in infants and children, and of enhancing cellular antioxidant capacity. Taurine has been widely used for treating various diseases such as cardiovascular diseases, diabetes, digestive diseases, nervous diseases and eye diseases. Due to the broad spectrum of applications, it is difficult to apply traditional bio-extraction method for producing taurine in a large scale. On this basis, nowadays, most taurine commercially available in the market is provided by chemical synthesis methods such as an ethanolamine process and an ethylene oxide process.

However, by-products such as ethylene glycol and ethanolamine will be formed in the chemical synthesis processes, and thus there is still a need for a new method for producing taurine with high productivity and less impurity.

SUMMARY

In view of this, in embodiments of the present disclosure, a method for producing taurine and a method for removing an impurity from a reaction system for producing taurine are provided.

In an aspect, the present disclosure provides in embodiments a method for producing taurine, including:
providing a reaction solution comprising alkali metal taurinate and/or alkali metal isethionate,
passing at least a portion of the reaction solution through a column of basic anion exchange resin, adsorbing anions of alkali metal taurinate and/or alkali metal isethionate to the basic anion exchange resin, and collecting an eluate comprising at least one impurity,
desorbing the anions of alkali metal taurinate and/or alkali metal isethionate from the basic anion exchange resin with an alkaline solution, and collecting a desorption liquid comprising alkali metal taurinate and/or alkali metal isethionate,
subjecting the desorption liquid comprising alkali metal taurinate to acidification or subjecting the desorption liquid comprising alkali metal isethionate to aminolysis and acidification, thereby obtaining taurine.

In another aspect, the present disclosure provides in embodiments a method for removing an impurity from a reaction system for producing taurine, including:
passing at least a portion of a reaction solution comprising alkali metal taurinate and/or alkali metal isethionate through a column of basic anion exchange resin, adsorbing anions of alkali metal taurinate and/or alkali metal isethionate to the basic anion exchange resin, thereby obtaining an eluate comprising the impurity,
desorbing the anions of alkali metal taurinate and/or alkali metal isethionate from the basic anion exchange resin with an alkaline solution, thereby obtaining a desorption liquid comprising alkali metal taurinate and/or alkali metal isethionate, and
feeding the desorption liquid into the reaction system for producing taurine.

Additional aspects and advantages of embodiments of present disclosure will be given in part in the following descriptions, become apparent in part from the following descriptions, or be learned from the practice of the embodiments of the present disclosure.

DETAILED DESCRIPTION

Objects, technical solutions and advantages of the present disclosure are described in detail below with reference to the embodiments. The embodiments described below are illustrative only and shall not be construed to limit the present disclosure. Unspecified techniques or conditions in embodiments or examples may be carried out in accordance with product specifications or according to common techniques or conditions in the art. Reagents or instruments used but not identified with manufacturers are common products commercially available.

When taurine is produced by the chemical synthesis, the ethanolamine method (i.e., taurine production from ethanolamine) has been gradually replaced by the ethylene oxide method (i.e., taurine production from ethylene oxide) having relative high synthesis yield, low cost and short period. However, in both methods, corresponding by-products are formed. For example, taurine is produced by the ethylene oxide method, a waste stock solution (also referred as a mother liquor) after separation of taurine still includes remained taurine and unreacted sodium sulfonate, and also includes ethylene glycol, ethanolamine and polymers thereof. Due to the presence of the impurities such as ethylene glycol, ethanolamine and polymers thereof, recycle of the mother liquor is limited, and productivity of taurine may be reduced and cost of the taurine production may be increased.

In an example, taurine is produced by the ethylene oxide method according to following formulas.

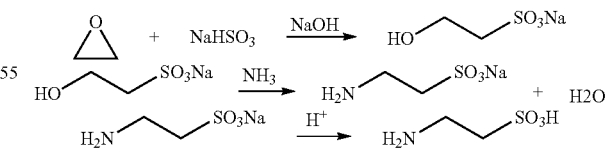

An addition reaction between ethylene oxide and sodium bisulfite occurs in the presence of sodium hydroxide as a catalyst, thus forming an intermediate, i.e., sodium isethionate. An aminolysis reaction between the sodium isethionate and ammonia will further take place, thus forming another intermediate, i.e., sodium taurinate. Sodium taurinate is neutralized under acidic conditions and thus taurine is produced.

In this method, side reactions of following formulas may occur.

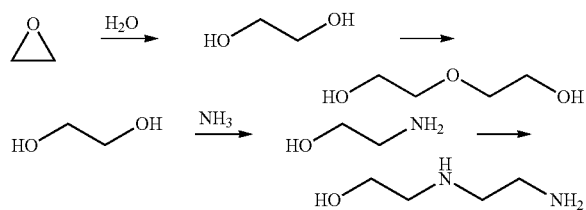

Ethylene oxide is reacted with water to produce ethylene glycol. Ethylene glycol may be polymerized to produce polyethylene glycol. Further, ethylene glycol may be reacted with ammonia (i.e., substitution reaction) to produce ethanolamine, and ethanolamine may be polymerized to produce polyethanolamine Since for example ethylene glycol and ethanolamine are easily soluble in water and have a high boiling point, it is difficult to remove ethylene glycol and ethanolamine by evaporation, such that these organic impurities remain in the mother liquor for a long period, thus negatively affecting a recovery ratio of the mother liquor, reducing the yield, and increasing the cost.

In the related art, an extraction process for recovering ethylene glycol and ethanolamine in the industrial taurine production with organic solvent is disclosed. Such a process introduces a large amount of the organic solvent into the mother liquor, and after separation, the process of recovering the organic phase via distillation and separating the by-products still requires a lot of energy. Moreover, the introduction of the original solvent may increase the risk of environmental pollution.

In view of this, the present disclosure provides in embodiments a method for producing taurine, which is able to remove impurities from a reaction system for producing taurine without the addition of original solvent, thus producing taurine with high purity and high yield.

In an aspect, the present disclosure provides in embodiments a method for producing taurine, including:

providing a reaction solution including alkali metal taurinate and/or alkali metal isethionate, passing at least a portion of the reaction solution through a column of basic anion exchange resin, adsorbing anions of alkali metal taurinate and/or alkali metal isethionate to the basic anion exchange resin, and collecting an eluate including at least one impurity, desorbing the anions of alkali metal taurinate and/or alkali metal isethionate from the basic anion exchange resin with an alkaline solution, and collecting a desorption liquid including alkali metal taurinate and/or alkali metal isethionate, subjecting the desorption liquid including alkali metal taurinate to acidification or subjecting the desorption liquid including alkali metal isethionate to aminolysis and acidification, thereby obtaining taurine.

Specifically, the reaction solution containing alkali metal taurinate is an aqueous solution having a concentration of alkali metal taurinate in a range of 0.01 to 99.99 wt %, and the reaction solution containing alkali metal isethionate is an aqueous solution having a concentration of alkali metal isethionate in a range of 0.01 to 99.99 wt %. High level of alkali metal taurinate or alkali metal isethionate may be used to prepare a taurine product with high purity, so as to meet the needs of high-end customers.

Specifically, the basic anion exchange resin is able to adsorb anions of both alkali metal taurinate and alkali metal isethionate, for example, in a case that mother liquor obtained after the separation of taurine includes both alkali metal taurinate and alkali metal isethionate, e.g. in the ethylene oxide method.

In an embodiment, the reaction solution is obtained by taurine production from ethylene oxide or ethanolamine.

In an embodiment, the reaction solution including alkali metal taurinate is prepared from aminolysis of alkali metal isethionate, and the reaction solution including alkali metal isethionate is prepared from a reaction between ethylene oxide and alkali metal bisulfite.

Specifically, the reaction solution including alkali metal taurinate is obtained from the aminolysis reaction, and the reaction solution including alkali metal isethionate is obtained from the addition reaction. In the addition reaction, an alkali metal may be added as a catalyst to facilitate the addition reaction. Alternatively, any suitable catalyst for such an addition reaction can be used. Moreover, the addition reaction occurs at a temperature in a range of 40 to 100° C., and a molar ratio of ethylene oxide to bisulfite is in a range of 1:(0.95 to 1). In the aminolysis reaction, a molar ratio of ammonia to alkali metal isethionate is adjusted in a range of (10 to 20): 1, and the aminolysis reaction takes place at a temperature from 200 to 300° C. and a pressure from 15 to 22 MPa. After the aminolysis reaction is accomplished, the pressure is rapidly reduced to a range from 0.1 to 1.5 MPa, and excess ammonia and heat are recovered.

In an embodiment, the method for producing taurine further includes separating taurine to obtain a stock solution (i.e., mother liquor) and recycling the stock solution to the reaction solution. In this embodiment, the stock solution is a solution including alkali metal taurinate and/or alkali metal isethionate.

Specifically, the mother liquor may be a waste solution after separation of taurine prepared by the ethanolamine method, and includes alkali metal taurinate and ethanolamine, or a waste solution after separation of taurine prepared by the ethylene oxide method, and includes one or more of alkali metal isethionate, alkali metal taurinate, ethylene glycol, polyethylene glycol, ethanolamine and polyethanolamine.

In an embodiment, the basic anion exchange resin is selected from any one from Amberlite IRA resin, quaternary ammonium anion exchange resin and tertiary ammonium anion exchange resin.

Specifically, the basic anion exchange resin is the Amberlite IRA resin or a 201*7 anion exchange resin.

In an embodiment, the reaction solution further includes an organic impurity and/or an electrically neutral impurity, and the organic impurity and/or the electrically neutral impurity is separated into the eluate.

In an embodiment, the organic impurity and/or electrically neutral impurity is selected from the group consisting of ethylene glycol, polyethylene glycol, ethanolamine, polyethanolamine and a combination thereof.

In an embodiment, the desorption liquid is recycled to the reaction solution.

Specifically, the desorption liquid is recycled to a mixed solution of ethylene oxide and alkali metal bisulfite, or to a solution including alkali metal isethionate which will be subjected to aminolysis.

In an embodiment, the alkaline solution is an aqueous alkali metal hydroxide solution, in which the alkali metal of the hydroxide is the same as that of alkali metal taurinate or of alkali metal isethionate.

For example, when alkali metal taurinate is sodium taurinate, the alkaline solution is a sodium hydroxide solution, and when alkali metal taurinate is potassium taurinate, the alkaline solution is a potassium hydroxide solution.

In an embodiment, before the at least a portion of the reaction solution passes through the column of the basic anion exchange resin, the method for producing taurine of the present disclosure further includes: diluting the reaction solution.

In an embodiment, alkali metal taurinate or alkali metal isethionate has a concentration in a range of 0.05 to 5 mol/L.

In an embodiment, a column temperature is controlled in a range of 25 to 90° C.

Specifically, the column temperature is in a range of 25 to 60° C., e.g., 25 to 35° C.

In an embodiment, the reaction solution passes through the resin at a flow rate from 2.0 to 3.0 BV/h.

In an embodiment, the collection of the eluate is stopped when pH of the eluate is monitored to rise to 12.5.

In an embodiment, the collection of the desorption liquid is stopped when pH of the desorption liquid is monitored to rise to 12.

In an embodiment, the desorption liquid is acidified by passing it through a column of acidic cation exchange resin, or by using an inorganic acid or an organic acid, or by applying an electrolytic method.

In an embodiment, the alkali metal is selected from the group consisting of lithium, sodium, potassium and a combination thereof.

In another aspect, the present disclosure provides in embodiments a method for removing an impurity from a reaction system for producing taurine, including:

passing at least a portion of a reaction solution including alkali metal taurinate and/or alkali metal isethionate through a column of basic anion exchange resin, adsorbing anions of alkali metal taurinate and/or alkali metal isethionate to the basic anion exchange resin, thereby obtaining an eluate including the impurity, desorbing the anions of alkali metal taurinate and/or alkali metal isethionate from the basic anion exchange resin with an alkaline solution, thereby obtaining a desorption liquid including alkali metal taurinate and/or alkali metal isethionate, and feeding the desorption liquid into the reaction system for producing taurine.

In an embodiment, the reaction system for producing taurine includes a system for producing taurine by the ethylene oxide method and a system for producing taurine by the ethanolamine method.

In an embodiment, the feedback of the desorption liquid to the reaction system for producing taurine specifically refers to the system for producing taurine by the ethylene oxide method or the system for producing taurine by the ethanolamine method.

In an embodiment, the impurity includes an organic impurity and/or an electrically neutral impurity.

Specifically, the organic impurity and/or electrically neutral impurity is selected from the group consisting of ethylene glycol, polyethylene glycol, ethanolamine, polyethanolamine and a combination thereof.

In an embodiment, the reaction system for producing taurine is subjected to following steps:

a) reacting ethylene oxide with alkali metal bisulfite, and obtaining a solution including alkali metal isethionate, b) performing aminolysis between the solution of alkali metal isethionate and an ammonia solution, obtaining a solution including alkali metal taurinate, and removing excess ammonia from the solution including alkali metal taurinate, and c) acidifying the solution including alkali metal taurinate, and obtaining taurine by separation.

Specifically, the desorption liquid is returned to any of steps a) to c).

Beneficial effects of the embodiments of the present disclosure are as follows.

With the method according to embodiments of the present disclosure, in the processes of producing taurine or recycling the mother liquor, the impurities is removed by the column of basic anion exchange resin, without introducing an organic solvent which is applied for impurity removal in the related art. Therefore, the method of the present disclosure can improve yield of the taurine product, simplify production processes, and reduce energy consumption, which is beneficial to environmental protection.

All of the above described features and advantages for the method for producing taurine in the above aspect are also applicable to the method for removing an impurity from a reaction system for producing taurine, which will not be elaborated in detail herein.

In addition, the technical features involved in the various embodiments described in the present disclosure may exist in any combination as long as they do not have opposite limitations.

The present disclosure is further described in accordance with following examples.

EXAMPLES

Example 1

In this example, preparation and further treatment for a column of basic anion resin are described.

Pre-Treatment for the Column

Amberlite IRA basic anion resin was added into an exchange column in a wet process. Water was introduced in as a top layer on the resin, which has a height of 20% of a total height of the column. The column was gently percussed to make the resin dense. Under nitrogen protection, a sodium hydroxide solution of 2 BV and 0.1 mol/L passed through the resin in a forward direction at a flow rate of 2.0 BV/h. Residual anions of sodium hydroxide not absorbed by the resin in the column were washed with deionized water, and pH of an effluent from the column was monitored. Washing may be stopped when the pH of the effluent is detected in a range of 8.0±0.5.

Regeneration Treatment for the Column The basic anion exchange column obtained as described above was washed with deionized water until the pH value was detected to be about 7. A sodium hydroxide solution of 2 BV and 0.1 mol/L passed through the resin in a forward direction at a flow rate of 2.0 BV/h again. Residual anions of sodium hydroxide not absorbed by the resin in the column were washed with deionized water, and pH of an effluent from the column was monitored. Regeneration may be regarded as completed when the pH of the effluent is detected in a range of 8.0±0.5.

Eluate obtained during the regeneration may be delivered to a storage tank for the sodium hydroxide solution which may be used as a catalyst or a hydroxyl-protecting agent for an addition reaction of the ethylene oxide and sodium bisulfite.

Besides Amberlite IRA basic anion resin, quaternary ammonium anion exchange resin or tertiary ammonium anion exchange resin may be used to obtain a corresponding column.

Example 2

In this example, a capacity of the basic anion resin for absorbing anions of alkali metal taurinate or a mixture of alkali metal taurinate and alkali metal isethionate is described below. Specifically, the alkali metal is sodium.

0.5 mol/L sodium taurinate solution or a mixed solution of 0.5 mol/L sodium taurinate solution and 0.5 mol/L sodium isethionate passed through different types of basic anion resin, i.e., Amberlite IRA resin, quaternary ammonium anion exchange resin or tertiary ammonium anion exchange resin, respectively, at a room temperature and at a flow rate of 1.0 BV/h. On this basis, the capacity of each of these resins for absorbing anions of sodium taurinate or the mixture of sodium taurinate and sodium isethionate was tested. As a result, it has been found that these resins, e.g., 207*7 resin (a quaternary ammonium resin) and Amberlite IRA resin available in the market have good adsorption capacity for the sodium taurinate or the mixture of sodium taurinate and sodium isethionate, for example with a high adsorption rate of more than 90%.

Moreover, for the alkali metal of alkali metal taurinate or alkali metal isethionate, potassium or other alkali metals may also be used. Tests were made to indicate that each resin as described above has a good adsorption capacity for both alkali metal taurinate and alkali metal isethionate.

Example 3

In this example, a solution as an equivalent to an industrial mother liquor after extracting taurine by the ethylene oxide method was prepared. Such a solution has a similar composition with the industrial mother liquor, i.e., is a mixed solution containing 14% sodium taurinate, 10% sodium isethionate, 5.5% ethanolamine, and 4.5% ethylene glycol.

Specifically, 270 g of ethylene glycol, 330 g of ethanolamine, 840 g of sodium taurinate and 600 g of sodium isethionate were taken and added into a 10 liter beaker, and purified water was added to until a final volume of the formed solution reached 5 L, thereby obtaining the solution containing 14% sodium taurinate, 10% sodium isethionate, 5.5% ethanolamine, and 4.5% ethylene glycol.

In other similar situations, solutions with different ratios of components can be prepared according to actual needs, all of which can achieve the technical effects designed by the present disclosure.

Example 4

In this example, the solution prepared in Example 3 was subjected to the column of Amberlite IRA basic anion exchange resin after pre-treatment or regeneration as described in Example 1 under different condition parameters such as a dilution ratio, a flow rate and a column temperature. Effects of the parameters on the adsorption capacity are described by means of the orthogonal experimental design.

Experiment 1

500 mL of the solution of Example 3 was taken and diluted with different dilution ratios. The dilution ratio refers to a ratio of a volume of the water used for dilution to a volume of the original solution, for example, when the dilution ratio is 2, it indicates that 1000 ml water is added to dilute 500 ml original solution.

The diluted solution passed through the resin column having a column temperature of 25° C. with a flow rate of about 2.0 BV/h, and an effluent (i.e., an eluate) discharged from an outlet of the column was collected. During the collection, pH of the effluent was monitored online at the outlet, and the collection was stopped when the detected pH was increased to about 12.5. The collected effluent includes water originally remained in the column, sodium hydroxide exchanged from the column, and ethylene glycol and ethanolamine, which may be collected for an addition reaction between ethylene oxide and sodium bisulfite and a process for activating resin. Sodium hydroxide solution of 0.1 mol/L passed through the resin in a forward direction at a flow rate of 2.0 BV/h to desorb the anions of the sodium taurinate and the sodium isethionate from the resin, and a desorption liquid discharged from an outlet of the column was collected. During the collection, pH of the desorption liquid was monitored online at the outlet, and the collection was stopped when the detected pH was suddenly increased to about 12. The desorption liquid includes relatively pure sodium taurinate and sodium isethionate. Such desorption liquid was subjected to aminolysis and acidification, thereby obtaining taurine. Contents of sodium taurinate, sodium isethionate, ethanolamine and ethylene glycol were detected for a diluted sample without passing through the column and the obtained effluent by chemical titration or liquid chromatography.

An elution rate (total amount in the eluate/total amount in the diluted sample without passing through the column) of ethylene glycol and ethanolamine, and an exchange rate (total amount in the desorption liquid/total amount in the diluted sample without passing through the column) of sodium taurinate and sodium isethionate are calculated according to the contents detected as above, and recorded in Table 1 as shown below.

TABLE 1

| Dilution Ratio | Elution Rate | | Exchange Rate | |
| --- | --- | --- | --- | --- |
| | ethylene glycol (%) | ethanolamine (%) | sodium taurinate (%) | sodium isethionate (%) |
| 0 | 99.1 | 99.4 | 7.9 | 10.6 |
| 2 | 99.3 | 97.8 | 70.5 | 62.7 |
| 4 | 99.4 | 99.3 | 92.6 | 89.5 |
| 6 | 98.2 | 99.1 | 85.7 | 79.6 |
| 8 | 99.5 | 98.3 | 85.2 | 80.9 |

As shown in Table 1, when the column temperature is 25° C. and the flow rate is 2.0 BV/h, the dilution ratio almost has no effect on the elution rates of ethylene glycol and ethanolamine. However, the exchange rates of sodium taurinate and sodium isethionate are changed with different dilution ratios. When the dilution ratio is 4, the exchange rates of sodium taurinate and sodium isethionate are at a higher level.

Experiment 2

500 mL of the solution of Example 3 was taken and diluted with a dilution ratio of 4. The diluted solution passed through the resin column having a column temperature selected from a range from 10 to 90° C. at a flow rate of about 2.0 BV/h, and an effluent (i.e., an eluate) discharged from an outlet of the column was collected. During the collection, pH of the effluent was monitored online at the outlet, and the collection was stopped when the detected pH was increased to about 12.5. The collected effluent includes water originally remained in the column, sodium hydroxide exchanged from the column, and ethylene glycol and ethanolamine, which may be collected for an addition reaction between ethylene oxide and sodium bisulfite and a process for activating resin. Sodium hydroxide solution of 0.1 mol/L passed through the resin in a forward direction at a flow rate of 2.0 BV/h to desorb the anions of the sodium taurinate and the sodium isethionate from the resin, and a desorption liquid discharged from an outlet of the column was collected. During the collection, pH of the desorption liquid was monitored online at the outlet, and the collection was stopped when the detected pH was suddenly increased to about 12. The desorption liquid includes relatively pure sodium taurinate and sodium isethionate. Such desorption liquid was subjected to aminolysis and acidification, thereby obtaining taurine. Contents of sodium taurinate, sodium isethionate, ethanolamine and ethylene glycol were detected for a diluted sample without passing through the column and the obtained effluent by chemical titration or liquid chromatography.

An elution rate (total amount in the eluate/total amount in the diluted sample without passing through the column) of ethylene glycol and ethanolamine, and an exchange rate (total amount in the desorption liquid/total amount in the diluted sample without passing through the column) of sodium taurinate and sodium isethionate are calculated according to the contents detected as above, and recorded in Table 2 as shown below.

TABLE 2

| Column Temperature (° C.) | Elution Rate | | Exchange Rate | |
| --- | --- | --- | --- | --- |
| | ethylene glycol (%) | ethanol-amine (%) | ethylene glycol (%) | ethanol-amine (%) |
| 10 | 99.2 | 98.4 | 46.2 | 28.7 |
| 25 | 99.3 | 97.8 | 92.6 | 89.5 |
| 35 | 99.4 | 99.2 | 92.8 | 91.8 |
| 45 | 99.5 | 99.1 | 93.2 | 93.5 |
| 60 | 99.1 | 99.2 | 93.7 | 92.7 |
| 90 | 99.5 | 99.4 | 90.2 | 89.7 |

As shown in Table 2, when the dilution ratio is 4 and the flow rate is 2.0 BV/h, the column temperature almost has no effect on the elution rates of ethylene glycol and ethanolamine. However, the exchange rates of sodium taurinate and sodium isethionate are changed with different column temperatures. When the column temperature is in a range of 25 to 60° C., the exchange rates of sodium taurinate and sodium isethionate are at a higher level. The temperature may be selected in a range of 25 to 35° C. to reduce energy consumption.

Experiment 3

500 mL of the solution of Example 3 was taken and diluted with a dilution ratio of 4. The diluted solution passed through the resin column having a column temperature of 25° C. at a flow rate selected from a range from 0.5 to 5.0 BV/h, and an effluent (i.e., an eluate) discharged from an outlet of the column was collected. During the collection, pH of the effluent was monitored online at the outlet, and the collection was stopped when the detected pH was increased to about 12.5. The collected effluent includes water originally remained in the column, sodium hydroxide exchanged from the column, and ethylene glycol and ethanolamine, which may be collected for an addition reaction between ethylene oxide and sodium bisulfite and a process for activating resin. Sodium hydroxide solution of 0.1 mol/L passed through the resin in a forward direction at the same flow rate with that of the diluted solution to desorb the anions of the sodium taurinate and the sodium isethionate from the resin, and a desorption liquid discharged from an outlet of the column was collected. During the collection, pH of the desorption liquid was monitored online at the outlet, and the collection was stopped when the detected pH was suddenly increased to about 12. The desorption liquid includes relatively pure sodium taurinate and sodium isethionate. Such desorption liquid was subjected to aminolysis and acidification, thereby obtaining taurine. Contents of sodium taurinate, sodium isethionate, ethanolamine and ethylene glycol were detected for a diluted sample without passing through the column and the obtained effluent by chemical titration or liquid chromatography.

An elution rate (total amount in the eluate/total amount in the diluted sample without passing through the column) of ethylene glycol and ethanolamine, and an exchange rate (total amount in the desorption liquid/total amount in the diluted sample without passing through the column) of sodium taurinate and sodium isethionate are calculated according to the contents detected as above, and recorded in Table 3 as shown below.

TABLE 3

| Flow rate (BV/h) | Elution Rate | | Exchange Rate | |
| --- | --- | --- | --- | --- |
| | ethylene glycol (%) | ethanol-amine (%) | ethylene glycol (%) | ethanol-amine (%) |
| 0.5 | 99.7 | 99.4 | 32.7 | 48.9 |
| 1.5 | 99.5 | 98.8 | 84.5 | 79.8 |
| 2.0 | 99.4 | 99.2 | 92.8 | 91.8 |
| 2.5 | 99.3 | 99.1 | 90.2 | 91.5 |
| 3.0 | 99.1 | 99.2 | 93.7 | 91.6 |
| 5.0 | 99.5 | 99.6 | 79.5 | 80.2 |

As shown in Table 3, when the dilution ratio is 4 and the column temperature is 25° C., the flow rate almost has no effect on the elution rates of ethylene glycol and ethanolamine. However, the exchange rates of sodium taurinate and sodium isethionate are changed with different flow rates. When the flow rate is in a range of 2.0 to 3.0 BV/h, the exchange rates of sodium taurinate and sodium isethionate are at a higher level.

Example 5

2000 mL of mother liquor including 5% sodium taurinate and 15% ethanolamine was taken after taurine produced by the industrial ethanolamine process was extracted. The mother liquor passed through the column of Amberlite IRA resin activated as described in Example 1 having a column temperature of 25° C. at a flow rate of about 2.0 BV/h, and an effluent (i.e., an eluate) discharged from an outlet of the column was collected. During the collection, pH of the effluent was monitored online at the outlet, and the collection was stopped when the detected pH was increased to about 12.5. The collected effluent includes water originally remained in the column, sodium hydroxide exchanged from the column and ethanolamine After the collection, ethanolamine may be used for an esterification process in the ethanolamine method for producing taurine, and sodium hydroxide may be used for a process for activating resin. Sodium hydroxide solution of 0.1 mol/L passed through the resin in a forward direction at a flow rate of 2.0 BV/h to desorb the anions of the sodium taurinate from the resin, and a desorption liquid discharged from an outlet of the column was collected. During the collection, pH of the desorption liquid was monitored online at the outlet, and the collection was stopped when the detected pH was suddenly increased to about 12. The desorption liquid includes relatively pure sodium taurinate. Obtained sodium taurinate solution was acidified by passing through a cation exchange (e.g., sulfonic acid type) column to obtain taurine, which was concentrated, recrystallized, filtrated and dried, thereby obtaining 83 g taurine product having a taurine content of 98% and a yield of 95.7%.

Example 6

2000 mL of sodium isethionate solution having a content of 10% was taken from the laboratory ethylene oxide method. The solution passed through the column of Amberlite IRA resin activated as described in Example 1 having a column temperature of 25° C. at a flow rate of about 2.0 BV/h, and an effluent (i.e., an eluate) discharged from an outlet of the column was collected. During the collection, pH of the effluent was monitored online at the outlet, and the collection was stopped when the detected pH was increased to about 12.5. The collected effluent includes water originally remained in the column, sodium hydroxide exchanged from the column, and ethylene glycol and ethanolamine, which may be collected for an addition reaction between ethylene oxide and sodium bisulfite and a process for activating resin. Sodium hydroxide solution of 0.1 mol/L passed through the resin in a forward direction at a flow rate of 2.0 BV/h to desorb the anions of the sodium isethionate from the resin, and a desorption liquid discharged from an outlet of the column was collected. During the collection, pH of the desorption liquid was monitored online at the outlet, and the collection was stopped when the detected pH was suddenly increased to about 12. The desorption liquid includes relatively pure sodium isethionate. Obtained sodium isethionate solution was concentrated to have a content of 35%, and 500 ml of the concentrated sodium isethionate solution was taken in a high-pressure autoclave, and further added with 600 ml of concentrated aqueous ammonia (28%). The reaction was carried out for 2 h at an autoclave temperature of 250° C. and a pressure of 18 MPa Ammonia was removed from the system and obtained mixture was cooled down and diluted by 10 times, and further acidified by passing through a sulfonic cation exchange resin to obtain a taurine solution, which was concentrated, recrystallized, filtrated and dried, thereby obtaining 137 g taurine product having a taurine content of 98% and a yield of 91%.

Example 7

In this example, effects of introducing the mother liquor prepared in Example 3 or the mother liquor treated with the column into the reaction system for producing taurine on the yield are analyzed.

1 L of sodium isethionate solution (3.5 mol/L) and 0.9 L of concentrated ammonia water (30%) were added in each of two 5 L autoclaves. In a first autoclave, 1 L of the solution of Example 3 was added. A treated solution obtained from Example 4 (e.g. the effluent obtained under conditions of the dilution ratio of 4, the flow rate of 2.0 BV/h and the column temperature of 25° C., in such a case 99.4% of ethylene glycol and 99.3% of ethanolamine are removed from untreated mother liquor) was concentrated to have the same content of sodium isethionate with the solution prepared in Example 3, and 1 L of the concentrated solution was added in a second autoclave. The pH values of both solutions in the first and second autoclaves were adjusted to 12 with sodium hydroxide, and the reaction was carried out for 2 h at a temperature of 240° C., and a pressure of 20 Mpa. After reaction, excess ammonia was removed, the solutions are further treated to obtain taurine at the same condition and amounts of generated taurine of both autoclaves were measured.

In the first autoclave, 4.45 mol taurine is obtained and a conversion from sodium isethionate to taurine is 80%. In the second autoclave, 5.15 mol taurine is obtained and a conversion from sodium isethionate to taurine is 95%.

It can be seen from Example 7 that ethylene glycol and ethanolamine are present in the reaction system, which affects the conversion of sodium isethionate. When the mother liquor is further subjected to the column of the present disclosure, most of ethylene glycol and ethanolamine are removed, and the conversion is increased by 15%.

It will be appreciated that related features in the above described devices may be referenced to each other. In addition, terms such as "first" and "second" are used herein for distinguishing features, embodiments or aspects described in the present disclosure, and are not intended to indicate or imply relative importance or significance.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples" in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for producing taurine, comprising:
    providing a reaction solution comprising alkali metal taurinate and/or alkali metal isethionate,
    passing at least a portion of the reaction solution through a column of basic anion exchange resin, adsorbing anions of alkali metal taurinate and/or alkali metal isethionate to the basic anion exchange resin, and collecting an eluate comprising at least one impurity,
    desorbing the anions of alkali metal taurinate and/or alkali metal isethionate from the basic anion exchange resin with an alkaline solution, and collecting a desorption liquid comprising alkali metal taurinate and/or alkali metal isethionate,
    subjecting the desorption liquid comprising alkali metal taurinate to acidification or subjecting the desorption liquid comprising alkali metal isethionate to aminolysis and acidification, thereby obtaining taurine.

2. The method according to claim 1, wherein the reaction solution is obtained by taurine production from ethylene oxide or ethanolamine.

3. The method according to claim 1, wherein
the reaction solution comprising alkali metal taurinate is prepared from aminolysis of alkali metal isethionate, or
the reaction solution comprising alkali metal isethionate is prepared from a reaction between ethylene oxide and alkali metal bisulfite.

4. The method according to claim 1, further comprising:
separating taurine to obtain a stock solution, wherein the stock solution is a solution comprising alkali metal taurinate and/or alkali metal isethionate, and
recycling the stock solution to the reaction solution.

5. The method according to claim 1, wherein the basic anion exchange resin is selected from any one from quaternary ammonium anion exchange resin and tertiary ammonium anion exchange resin.

6. The method according to claim 1, wherein the impurity comprises an organic impurity and/or an electrically neutral impurity.

7. The method according to claim 6, wherein the organic impurity and/or electrically neutral impurity is selected from the group consisting of ethylene glycol, polyethylene glycol, ethanolamine, polyethanolamine and a combination thereof.

8. The method according to claim 1, and further comprising:
passing at least a portion of the collected desorption liquid through the column of basic anion exchange resin, absorbing anions of alkali metal taurinate and/or alkali metal isethionate to the basic anion exchange resin, and collecting an eluate comprising at least one impurity; and
desorbing the anions of alkali metal taurinate and/or alkali metal isethionate from the basic anion exchange resin with an alkaline solution, and collecting the collected desorption liquid.

9. The method according to claim 1, wherein the alkaline solution is an aqueous alkali metal hydroxide solution, wherein the alkali metal of the hydroxide is the same as that of the alkali metal taurinate or of the alkali metal isethionate.

10. The method according to claim 1, wherein before the at least a portion of the reaction solution passes through the column of the basic anion exchange resin, the method further comprises: diluting the reaction solution.

11. The method according to claim 10, wherein the alkali metal taurinate or the alkali metal isethionate has a concentration in a range of 0.05 to 5 mol/L before or after diluting the reaction solution.

12. The method according to claim 1, wherein a temperature of the column of basic anion exchange resin is controlled in a range of 25 to 90° C.

13. The method according to claim 1, wherein the reaction solution passes through the resin at a flow rate from 2.0 to 3.0 BV/h.

14. The method according to claim 1, wherein the collection of the eluate is stopped when the pH of the eluate is monitored to rise to 12.5.

15. The method according to claim 1, wherein the collection of the desorption liquid is stopped when the pH of the desorption liquid is monitored to rise to 12.

16. The method according to claim 1, wherein the desorption liquid is acidified by passing it through a column of acidic cation exchange resin, or by using an inorganic acid or an organic acid, or by applying an electrolytic method.

17. The method according to claim 1, wherein the alkali metal is selected from the group consisting of lithium, sodium, potassium and a combination thereof.

18. A method for removing an impurity from a reaction system for producing taurine, comprising:
passing at least a portion of a reaction solution comprising alkali metal taurinate and/or alkali metal isethionate through a column of basic anion exchange resin, adsorbing anions of alkali metal taurinate and/or alkali metal isethionate to the basic anion exchange resin, thereby obtaining an eluate comprising the impurity,
desorbing the anions of alkali metal taurinate and/or alkali metal isethionate from the basic anion exchange resin with an alkaline solution, thereby obtaining a desorption liquid comprising alkali metal taurinate and/or alkali metal isethionate, and
feeding the desorption liquid into the reaction system for producing taurine.

19. The method according to claim 18, wherein the impurity comprises an organic impurity and/or an electrically neutral impurity.

20. The method according to claim 18, wherein the reaction system for producing taurine comprises the following steps:
a) reacting ethylene oxide with an alkali metal bisulfite, and obtaining a solution comprising an alkali metal isethionate,
b) performing aminolysis between the solution comprising alkali metal isethionate and an ammonia solution, obtaining a solution comprising an alkali metal taurinate, and removing excess ammonia from the solution comprising alkali metal taurinate, and
c) acidifying the solution comprising alkali metal taurinate, and obtaining taurine by separation,
wherein the desorption liquid is returned to any of steps a) to c).

* * * * *